United States Patent [19]

Stanford et al.

[11] Patent Number: 5,599,545
[45] Date of Patent: Feb. 4, 1997

[54] MYCOBACTERIUM AS ADJUVANT FOR ANTIGENS

[75] Inventors: John L. Stanford, Marden; Graham Arthur W. Rook, Suffolk, both of United Kingdom

[73] Assignee: University College London, United Kingdom

[21] Appl. No.: 441,785

[22] Filed: May 16, 1995

Related U.S. Application Data

[63] Continuation of Ser. No. 50,282, filed as PCT/GB91/01969, abandoned.

[30] Foreign Application Priority Data

Nov. 8, 1990 [GB] United Kingdom .................. 9024282
Jul. 17, 1991 [GB] United Kingdom .................. 9115410

[51] Int. Cl.$^6$ ................................................... A61K 39/04
[52] U.S. Cl. ................. 424/282.1; 424/93.4; 424/248.1; 435/253.1
[58] Field of Search ............................ 424/184.1, 185.1, 424/248.1, 93.1, 93.2, 93.4, 282.1; 514/28; 530/350, 395, 868; 435/253.1

[56] References Cited

U.S. PATENT DOCUMENTS

| 3,956,481 | 5/1976 | Jolles et al. ................................. 424/92 |
| 4,036,953 | 7/1977 | Adam et al. ................................. 424/92 |
| 4,724,144 | 2/1988 | Rook et al. ................................. 424/88 |

FOREIGN PATENT DOCUMENTS

| WO85/03639 | 8/1985 | WIPO ............................. A61K 39/04 |
| 8505034 | 11/1985 | WIPO ............................. A61K 35/74 |
| 90072935 | 7/1990 | WIPO ............................. A61K 39/02 |
| 9101751 | 2/1991 | WIPO ............................. A61K 39/04 |

OTHER PUBLICATIONS

Herbert, W. J. in Handbook of Experimental Immunology, 2nd edition, edited by D. M. Weir (1973), "Mineral–oil adjuvants and the immunization of laboratory animals", Appendix 2, pp. A2.1–A2.14.

Ganapati et al: "A piot study of three potential vaccines for leprosy in Bonbay", International Journal of Leprosy and Other Mycobacterial Diseases, vol. 57, No. 1, Mar. 1989, pp. 33–37, see the summary.

Audibert, F., et al., Immunology Today 14(6):281–284 (1993), "Adjuvants: current status, clinical perspectives and future prospects."

R. G. White et al., Immunology 7:158–171 (1964), "Correlation of adjuvant activity and chemical structure of Wax D fractions of mycobacteria".

R. G. White, International Symposium on Adjuvants of Immunity, Symp. Series Immunobiol. Stand. 6: 49–58, "Characterization of microbacterial components of adjuvant mixtures".

*Primary Examiner*—Thomas M. Cunningham
*Attorney, Agent, or Firm*—Cushman Darby & Cushman IP Group of Pillsburg Madison & Sutro LLP

[57] ABSTRACT

Immunoregulatry material from a mycobacterium other an *M. tuberculosis*, especially killed cells of *M. vaccae*, is an advantageous adjuvant for administration with antigens (including allergens).

10 Claims, No Drawings

MYCOBACTERIUM AS ADJUVANT FOR ANTIGENS

This is a continuation of application Ser. No. 08/050,282, filed on May 7, 1993, which was abandoned upon the filing hereof.

The present invention relates to carriers, and more particularly adjuvants, for antigens (including allergens), or use in vaccination, and other ways of altering, in a favorable way, the immune response to an antigen.

Killed cells of *M. vaccae* are known to be useful as immunotherapeutic agents in mycobacterial diseases such as tuberculosis and leprosy (see GB-A-2156673). This known use of *M. vaccae* may rely upon the stimulation of T-cell mediated immunity to endogenous antigens of *M. vaccae*. Killed cells of *M. vaccae* are also useful in the treatment of various autoimmune diseases including rheumatoid arthritis, ankylosing spondylitis and Reiter's syndrome (see PCT/GB 85/00183).

The present invention is founded upon the surprising observation that killed cells of *M. vaccae* can be used to stimulate and/or modify in a favorable way the immune response to antigens which are not endogenous to *M. vaccae*.

The immune response to an antigen has two distinct aspects: (1) selection of an epitope (antigen fragment) as an initiator of, and target for, the response; and (2) selection of a particular immune response mechanism as the response directed against the particular epitope selected. Current methods of stimulating the immune response, e.g. vaccination, have generally concentrated on the first aspect, but it has become clear, in the light of recent research, that it is essential that the immune response shall be stimulated or modified to a favorable way, since it is possible to modify the immune response unfavorably, leading for example to increased susceptibility to infection. One of the surprisingly beneficial properties of killed cells of *M. vaccae* in that they promote selection of a favorable immune response mechanism.

It is known that, at least in the mouse (see, e.g. Mosmann & Moore, Immunology Today, 1991, A49–A53), different T-cell subsets have different patterns of cytokine secretion. $T_H2$ cells express interleukin(IL)-4, IL-5 and IL-10, whereas $T_H1$ cells produce IL-2,γ-interferon (IFN-γ) and lymphotoxin. The $T_H2$ cells are involved in the pattern of immune responses seen in, e.g., asthma, pollen allergies, and eczema, while $T_H1$ cells are involved in the pattern used in killing intracellular parasites. It appears that killed cells of *M. vaccae* promote the immune response characteristic of $T_H1$ cells.

Conversion of the T cell component of the response to allergens from the $T_H2$ pattern to the $T_H1$ pattern reduces or terminates symptoms of conditions such as asthma, hay fever, and atopic eczema, by reducing production of IgE, reducing recruitment of eosinophils and mast cells to the inflamed site, and greatly increasing the antigen concentration required to trigger a response (because the $T_H1$ response requires a much higher concentration of antigen to be triggered than the $T_H2$ response). Consequently the levels of allergen in the environment become insufficient to trigger symptoms.

It also appears that killed cells of *M. vaccae* may promote the immune response characteristic of $T_H1$ cells, and in the case of autoantigens, enhance reduction of the response via the immunoregulatory network.

The beneficial effect of using killed *M. vaccae* as an adjuvant may also be associated with the 65 kDa mycobacterial heat shock protein (hsp 65) described by Young et al. "Stress proteins are immune targets in leprosy and tuberculosis", Proc. Natl. Acad. Sci. U.S.A. 85 (1988), pp4267–4270 in form obtained from *M. bovis*. The preferred autoclaved *M. vaccae* cells used in the present invention as described below are believed to provide an effective package of adjuvant, hsp 65 and other substances.

The immunoregulatory material derived from *M. vaccae* or another mycobacterium other than *M. tuberculosis* may be administered with or separately from the antigen exogenous to the mycobacterium to achieve an improved response to the antigen.

*M. tuberculosis* is the causative agent of tuberculosis and an avirulent variant of it is used in the production of the BCG used vaccine against tuberculosis in immunization programmes throughout the world. Immunoregulatory material from *M. tuberculosis* should not be used in accordance with the present invention in order to avoid compromising the use of BCG vaccine by inducing tuberculin test positivity or reducing the subsequent efficacy of BCG. For these reasons the use of immunoregulatory material from *M. tuberculosis* is excluded from the present invention.

It is believed that material from mycobacterial species other than *M. tuberculosis* might be useful in accordance with the present invention. However, especially as it is already a known immunotherapeutic agent, immunoregulatory material from *M. vaccae* is currently preferred.

The invention accordingly provides a product comprising immunoregulatory material derived from a mycobacterium other than *M. tuberculosis* and an antigen exogenous to the mycobacterium as a combined preparation for simultaneous, separate or sequential use for promoting T cell-mediated response to said antigen.

The product of the invention conveniently, and therefore preferably, comprises dead cells of *M. vaccae*, most preferably cells which have been killed by autoclaving or by irradiation. The product normally comprises more than $10^8$ microorganisms per ml of diluent, and preferably from $10^8$ to $10^{11}$ killed *M. vaccae* microorganisms per ml of diluent.

The diluent may be pyrogen-free saline for injection alone, or a borate buffer of pH 8.0. The diluent should be sterile. A suitable borate buffer is:

| | |
|---|---|
| $Na_2B_4O_7.10H_2O$ | 3.63 g |
| $H_3BO_3$ | 5.25 g |
| NaCl | 6.19 g |
| Tween 80 | 0.0005% |
| Distilled Water | to 1 liter |

The preferred strain of *M. vaccae* is one denoted R877R isolated from mud samples from the Lango district of Central Uganda (J. L. Stanford and R. D. Paul, Ann. Soc. Belge Med, Trop. 1973, 53 141–389). The strain is a stable rough variant and belongs to the aurum sub-species. It can be identified as belonging to *M. vaccae* by biochemical and antigenic criteria (R. Bonicke, S. E. Juhasz., Zentr albl. Bakteriol. Parasitenkd. Infection skr. Hyg. Abt. 1, Orig., 1964, 192, 133).

The strain denoted R877R has been deposited under the Budapest Convention at the National Collection of Type Cultures (NCTC) Central Public Health Laboratory, Colindale Avenue, London NW9 5HT, United Kingdom on Feb. 13, 1984 under the number NCTC 11659.

For the preparation of the product of the invention, the microorganism *M. vaccae* may be grown on a suitable solid medium. A modified Sauton's liquid medium is preferred (S. V. Boyden and E. Sorkin., J. Immunol, 1955 75, 15) solidified with agar. Preferably the solid medium contains 1.3% agar. The medium inoculated with the microorganisms is incubated aerobically to enable growth of the microorganisms to take place, generally at 32° C. for 10 days. The organisms are harvested, then weighed and suspended in a diluent. The diluent may be unbuffered saline but is preferably borate-buffered and contains a surfactant such as Tween 80 as described above. The suspension is diluted to give 200 mg of microorganism/ml. For further dilution, borate buffered saline is preferably used so that the suspension contains 10 mg wet weight of microorganisms/ml of diluent. The suspension may then be dispensed into suitable multidose vials (e.g. 1 ml). Although the microorganisms in the vials may be killed using irradiation, e.g. from $^{60}$Cobalt at a dose of 2.5 megarads, or by any other means, for example chemically, it is preferred to kill the microorganisms by autoclaving, for example at 10–15 psig (69–104 kPa) for 10–15 minutes (115°–125° C.). It has been discovered, unexpectedly, that autoclaving yields a more effective preparation than irradiation.

Extracts or fractioned portions of the microorganisms can also be used provided, of course, they have the required adjuvant effect.

The immunotherapeutic product of the invention comprises an association of an effective, non-toxic immunomodifying amount of an immunoregulatory material from a mycobacterium other than *M. tuberculosis*, especially *M. vaccae*, and of an effective, non-toxic, immunity-stimulating amount of an antigen exogenous to the mycobacterium.

The exogenous antigen may be any antigen against which it is desired to stimulate T-cell mediated immunity or to alter the nature of the T-cell response, to achieve palliation or cure of the infection or other condition to be treated. Examples include antigens associated with diseases at present regarded as having an autoimmune aetiology such as multiple sclerosis, antigens associated with chronic viral infections such as hepatitis, bovine spongiform encephalopathy (BSE), and myoencephalitis (ME), antigens associated with cryptic parasite infections such as leishmaniasis and trypanosomiasis, and allergens (e.g. those present in pollens, animal dander, and house dust mite) responsible for such conditions as hayfever, asthma, food allergy and eczema. The immunotherapeutic product of the invention incorporating the appropriate exogenous antigen may be used prophylactically or therapeutically.

The exogenous antigen may be produced by any conventional technique, such as by culture and killing or attenuating the disease organism to provide a killed or attenuated vaccine, by separation and purification of the antigen, with optional chemical modification thereof, from a disease organism or, in the case of proteinaceous antigens, by expression of a gene encoding the antigenic protein in a suitable recombinant organism.

The exogenous antigen may be combined with the immunoregulatory mycobacterial material by admixture, chemical conjugation or adsorption using conventional techniques. Alternatively the exogenous antigen may be produced by expression of an exogenous gene (for instance contained within a plasmid, cosmid, viral or other expression vector or inserted into the genome of the mycobacteria) in the mycobacteria from which the immunoregulatory material is also produced. Thus, for instance, recombinant *M. vaccae* may be cultured so as to achieve expression of the exogenous antigen and then killed and processed as described above, or under such conditions appropriately modified to preserve the biological activity of the exogenous antigen, to provide an immunoregulatory material containing the exogenous antigen. Techniques for obtaining and expressing such exogenous genes are conventional.

The therapeutic agent is in general administered by injection in a volume in the range 0.1–0.2 ml, preferably 0.1 ml, given intradermally. A single dosage will in general contain from $10^7$ to $10^{10}$ killed *M. vaccae* microorganisms. It is preferred to administer to patients a single dose containing $10^8$ to $2 \times 10^9$ killed *M. vaccae*. However, the dose may be repeated depending on the condition of the patient.

The amount of exogenous antigen administered in association with the *M. vaccae* is in general the same amount as has previously been used when the given antigen has been administered to provide an immune response. In the case of antigens involved in hay fever and asthma, the required dosage depends on the manner in which the antigen is extracted and specific dosages which are generally applicable cannot be given, although therapeutic preparations containing such antigens are well known, see the article on "Desensitising vaccines", Brit. Med. J. 293 (1986) p.948. For other types of antigen not involved in hay fever or asthma, the usual dosage is in the range of 0.1 to 5 µg.

The therapeutic agent may be administered with the antigen, typically in admixture, but it is within the scope of the invention to administer, e.g. by injection, first the therapeutic agent, e.g. killed cells of *M. vaccae*, and then, into the same site, the exogenous antigen.

Although the therapeutic agent will generally be administered by intradermal injection, other routes, e.g. oral administration, can also be used.

The invention includes within its scope a method of treatment of the human or animal body which comprises administering an effective non-toxic amount of immunoregulatory material derived from a mycobacterium other than *M. tuberculosis* and, with or following the said material, of an antigen exogenous to the mycobacterium to a human or animal in need of T-cell mediated immunity against the exogenous antigen or otherwise in need of the pattern of T-cell mediated response against the exogenous antigen promoted by the said immunoregulatory material.

The invention further provides the use, in the manufacture of an immunotherapeutic composition for use in treatment of the human or animal body by promoting the T-cell mediated response to an exogenous antigen, of immunoregulatory material derived from a mycobacterium other than *M. tuberculosis*, and pharmaceutical formulations comprising an association of the said immunoregulatory material and an antigen exogenous to the mycobacterium and one or more diluents or carriers therefor.

The pharmaceutical formulation can contain further ingredients such as additional adjuvants, preservatives, stabilisers etc. It may be supplied in sterile injectable liquid form or in sterile freeze-fried form which is reconstituted prior to use.

The following Example illustrates the invention.

EXAMPLE

*M. vaccae* NCTC 11659 is grown on a solid medium comprising modified Sauton's medium solidified with 1.3% agar. The medium is inoculated with the microorganism and incubated for 10 days at 32° C. to enable growth of the microorganism to take place. The microorganisms are then harvested by gently scraping the surface of the agar and weighed (without drying) and suspended in M/15 borate buffered saline at pH8 to give 10 mg of microorganisms/ml of saline. The suspension is dispensed into 5 ml vials, and then autoclaved for 15 minutes at 15 psi (104 kPa) and about 120° C. to kill the microorganisms. This is then dispensed into suitable multidose vials. After cooling, 1/10th volume of exogenous antigen (at the standard concentration of 2 µg/ml) is added. The therapeutic agent thus produced is stored at 4° C. before use. A single dose consists of 0.1 ml of the suspension, which should be shaken vigorously immediately before use, containing 1 mg wet weight of M. vaccae and 0.02 µg of exogenous antigen. The dose is given by intradermal injection normally over the left deltoid muscle.

Only one dose is normally required. The patient should not receive high dose steroids or other immuno-suppressive therapy. Up to six months may elapse before the beneficial effect becomes apparent.

We claim:

1. An aqueous non-emulsified composition comprising killed cells of *Mycobacterium vaccae,* an antigen exogenous to mycobacteria and one or more diluents or carriers therefor.

2. The composition of claim 1, wherein the exogenous antigen is produced by expression of an exogenous gene in recombinant *M. vaccae*.

3. The composition of claim 1, wherein the *M. vaccae* is chemically conjugated to the exogenous antigen.

4. The composition of claim 1, wherein the *M. vaccae* is killed by heat, chemical agents or irradiation.

5. The composition of claim 1, wherein the *M. vaccae* is killed by autoclaving.

6. The composition of claim 1, wherein the *M. vaccae* is the strain deposited at the National Collection of Type Cultures (NCTC) Central Public Health Laboratory, Colindale Avenue, London NW9 5HT, United Kingdom on Feb. 13, 1984 under the number NCTC 11659.

7. The composition of claim 1 comprising per dose $10^7$ to $10^{10}$ *M. vaccae* organisms.

8. A method of stimulating T-cell immunity in a mammal comprising administering to said mammal an effective non-toxic amount of the composition of any one of claims 1–7.

9. An aqueous non-emulsified suspension comprising killed cells of *Mycobacterium vaccae* and an antigen exogenous to the mycobacterium as a combined preparation for simultaneous or sequential administration for promoting T-cell mediated response to said antigen.

10. A method of stimulating T-cell immunity in a mammal comprising simultaneously or sequentially administering to said mammal an aqueous non-emulsified suspension comprising killed cells of *Mycobacterium vaccae* and an antigen exogenous to the mycobacterium.

* * * * *